United States Patent [19]

Schnaper et al.

[11] Patent Number: 4,771,125
[45] Date of Patent: Sep. 13, 1988

[54] HUMAN SOLUBLE IMMUNE RESPONSE SUPPRESSOR

[76] Inventors: H. William Schnaper, 12952 Mayerling Dr., Creve Coeur, Mo. 63146; Thomas M. Aune, 5 Moreland Pl., Glendale, Mo. 63122

[21] Appl. No.: 850,207

[22] Filed: Apr. 10, 1986

Related U.S. Application Data

[63] Continuation-in-part of Ser. No. 653,123, Sep. 21, 1984, Pat. No. 4,665,021.

[51] Int. Cl.⁴ ............................................. C07K 15/00
[52] U.S. Cl. ................................... 530/351; 530/350; 530/412; 530/416; 530/417; 530/418; 530/420; 435/68
[58] Field of Search ........ 530/350, 351, 412, 416–418, 530/420; 435/68

[56] References Cited

U.S. PATENT DOCUMENTS 4,665,032  5/1987  Laurence ............................ 530/380

OTHER PUBLICATIONS

Rich and Pierce, J. Immunol. 112(4), 1360–1368 (1974).
Aune and Pierce, J. Immunol. Meth. 53, 1–14 (1982).
Aune and Pierce, Lymphokines, vol. 9, E. Pick (ed.), Academic Press Inc., New York, 1984, pp. 257–277.
Aune et al., J. Immunol., 131(6), 2848–2852 (1983).
Webb et al., J. Immunol., 135(5), p.3238 (1985).
Schnaper et al., J. Immunol., 132(5), 2429–2435 (1984).
Aune, J. Immunol. Meth. 84,33 (1985).
Schnaper and Aune, Fed. Proc. 43, Abst. 2911, Mar. 1984.
Schnaper and Aune, Ped. Res. 18, Abst. 1637, May 1984.
Santoli et al., J. Exp. Med., 163, p. 8–40 (1986).
Aune et al., Prog. Clin. Biol. Res., 132B, 1983, pp. 335–344 (abst. only).
Aune et al., J. Immunol, 127(5) 1981, pp. 1828–1833.
Aune et al., T–Cell Hybridoma, ed. Joussig, 1985, pp. 210–215.
Wieder et al., J. Immunol, 132(2) 1984, pp. 556–558.
Irons et al., J. Immunol, 133(4) 1984, p. 2032.
Lederman et al., Clin. Exp. Immunol., 45(1) 1981, pp. 191–200.
Griene et al., J. Immunol., 126(3) 3/1981, pp. 1185–1191.
Fleisher et al., J. Immunol., 126(3) 3/1981, p. 1192.
Schnaper et al., J. Clin. Invest., 76, 1985, pp. 341–349.

Primary Examiner—John Kight
Assistant Examiner—Garnette D. Draper
Attorney, Agent, or Firm—Scott J. Meyer; James W. Williams, Jr.

[57] ABSTRACT

Human soluble immune response suppressor (SIRS) having a molecular weight of about 10,000 to 15,000, an isoelectric point of about 7 and a defined amino acid composition distinctly different from murine SIRS is produced from a culture of MOLT-4 cells.

3 Claims, 1 Drawing Sheet

HUMAN SOLUBLE IMMUNE RESPONSE SUPPRESSOR

CROSS-REFERENCE TO RELATED APPLICATION

This is a continuation-in-part of copending application Ser. No., 653,123, filed Sept. 21, 1984, now U.S. Pat. No. 4,665,021.

BACKGROUND OF THE INVENTION

This invention relates to a highly purified human lymphokine and, more particularly, to a lymphocyte factor which regulates antibody responses known as soluble immune response suppressor (SIRS).

Several nonspecific suppressor factors have been reported that are released by sensitized lymph node or spleen cells after challenge with the specific antigen or by spleen cells inoculated with Concanavalin A (Con A). One of these factors has been designated soluble immune response suppressor (SIRS). Rich and Pierce, *J. Immunol.* 112(4), 1360-1368 (1974). It is an early product of mouse spleen cells (Ly2, 3+ T cells) stimulated with antigen or Con A. In appropriate dilutions, it nonspecifically suppresses 5-day plaque-forming cell (PFC) responses to sheep red blood cells (SRBC) as well as antihapten antibody responses.

SIRS is known to be activated by macrophages or exogenous $H_2O_2$ to $SIRS_{ox}$, a reaction which is inhibited by catalase, levamisole and electron donors such as 2-mercaptoethanol (2-ME).

For further background information on the murine-derived SIRS, see the recent review article by Aune and Pierce, *J. Immunol. Methods* 53, 1-14 (1982); and their review paper in *Lymphokines*, Vol. 9, Ed. E. Pick, Academic Press, Inc., New York, 1984, pp. 257-277.

Recently, the purification and characterization of two molecular forms of murine SIRS having molecular weights of 21,500 and 14,000, respectively, was reported by Aune et al., *J. Immunol.* 131 (6), 2848-2852 (1983). Isoforms of SIRS with molecular weight of 11,000 are also disclosed by Webb et al., *J. Immunol.* 135, 3238 (1985), and in a U.S. patent application filed by Pierce and Webb, Oct. 22, 1985, Ser. No. 789,997, and jointly owned by a common assignee of the present application.

Human counterparts of murine SIRS also are known. See, for example, Schnaper, Pierce and Aune, *J. Immunol.* 132 (5), 2429-2435 (1984), which identifies the human factors as having 110,000-160,000 molecular weight when fractionated by chromatography on Sephacryl® S-200 gel using buffers of physiologic ionic strength, but suggests that fractionation in high ionic strength buffers may reduce the apparent molecular weight as in the case of murine SIRS.

In copending application Ser. No. 653,123, filed Sept. 21, 1984, now U.S. Pat. No. 4,665,021, a molecular weight of 10,000-15,000 is assigned to the latter fractionated human SIRS. According to the disclosure in said application, SIRS can also be fractionated from human urine samples of nephrotic patients, whereby its presence can serve as a useful diagnostic tool for screening for immune deficiency. See also Schnaper and Aune, *J. Clin. Invest.* 76, 341 (1985).

The specificity of assays for SIRS has been enhanced recently by utilization of monoclonal anti-murine SIRS antibodies which cross-react with human SIRS, and the identification of a characteristic elution pattern for human SIRS on high performance liquid chromatography (HPLC). See Aune, *J. Immunol. Meth.* 8, 33(1985).

DESCRIPTION OF THE INVENTION

In accordance with the present invention a novel human SIRS is provided which has a molecular weight of about 10,000-15,000, an isoelectric point of about 7 and an amino acid content as defined hereinafter which is significantly different from that of murine SIRS.

The novel human SIRS of this invention is preferably obtained from a culture of the human peripheral blood cell line MOLT-4. This cell line was originally derived from the peripheral blood of a patient with acute lymphoblastic leukemia. Further information on the origin and characteristics of this cell line can be had by reference to Minowada, *J. Nat. Cancer Inst.* 49, 891-895 (1972).

The MOLT-4 cell line is on deposit without restriction in the permanent collection of the American Type Culture Collection, Rockville, Md., under accession number ATCC CRL 1582. Samples of the cell line can be obtained by the public upon request to that depository.

The MOLT-4 cell line can be maintained in various conventional cell culture media. A preferred medium is RPMI 1640 supplemented with glutamine and 10% horse serum together with small but effective amounts of antibiotics such as penicillin and streptomycin. Incubation of the cells in the foregoing nutrient culture medium at 37° C. with a 5% overlay of $CO_2$ in air results in the production of significant levels of suppressive activity. RPMI 1640 and other conventional cell culture media can be used such as those described, for example, by Helen Morton, In Vitro 6, 89-108 (1970). These conventional cell culture media contain essential amino acids, mineral salts, vitamins and carbohydrates and are frequently fortified with mammalian sera. The SIRS is preferably recovered from the cell culture supernatant after an incubation or culture period of about 12 hours or greater.

Incubation of the MOLT-4 cells with Concanvalin A (Con A), recombinant leukocyte interferon ($IFN_\alpha A$) or immune interferon ($IFN_\gamma$) activates the cells to produce increased levels of SIRS, that is about a 3 to 10 fold increase. Enhancement of SIRS production also is obtained by treatment of the cell medium with the combination of Con A, cycloheximide, phorbol myristate acetate and actinomycin D.

Further purification of SIRS from the MOLT-4 cell supernates can be had by various protein purification procedures such as, for example, fractionation by precipitation with salts and solvents, dialysis, chromatography with ion-exchange and gel filtration resins, isoelectric focusing, affinity chromatography, high performance liquid chromatography (HPLC), electrophoresis and the like protein purification techniques. Since human SIRS has an isoelectric point of 7.0 and a molecular weight on the order of about 15,000, separation procedures based on isoelectric point, such as ion exchange chromatography or isoelectric focusing, separate SIRS from most contaminating proteins. Gel filtration and other types of separation based on molecular weight efficiently separate SIRS from the remaining contaminating protein. Reversed phase HPLC on a C-8 or C-18 column is used as a means of confirming purity and to examine microheterogeneity of SIRS.

One such illustrative purification sequence employs 40% ammonium sulfate precipitation, DEAE-Sephacyl® ion exchange chromatography, gel filtration with a Water's Protein Pac 125 column (silica gel) and HPLC on a Vydac C-18 reversed phase column. These column chromatography resins are all commercially available. Thus, DEAE-Sephacel is a bead-formed cellulose ion exchanger produced from high purity microcrystalline cellulose with diethylaminoethyl functional groups available from Pharmacia Fine Chemicals AB, Uppsala, Sweden. The C-18 (octadecyl) silica-based reversed phase Vydac HPLC column is available from The Separations Group, Hesperia Calif. The Water's Protein Pac 125 column is available from Water Associates, Milford, Mass.

A preferred purification method employs treatment with a Water's DEAE HPLC column prior to gel filtration with the Water's Protein Pac 125 column in the above purification sequence. The preferred method also includes dialysis of the protein after the salt fractionation step and after treatment with the DEAE-Sephacel ion exchange resin. Dialysis against about 0.025 M tris-HCl, pH 8.3, is preferred. Protein is preferably eluted from the DEAE-Sephacel column with a linear gradient from 0 to 0.5 M NaCl; from the DEAE HPLC column with an increasing gradient of NaCl to 0.3 M; and from the Vydac C-18 column with a linear gradient of 0-60% acetonitrile in 0 1% trifluoroacetic acid.

Fractionation of the MOLT-4 cell supernatant by gel chromatography with Sephacryl® S-200 using a phosphate buffered saline elution buffer (pH 7-7.4) indicated an active suppressive fraction at a molecular weight of about 110,000-160,000 daltons. However, when the chromatography was performed using 0.4 M pyridine/0.4 M acetic acid as the elution buffer, the molecular weight was estimated to be about 10,000-15,000. This phenomenon is similar to the results with SIRS from other sources and is believed to represent decreased aggregation or binding of SIRS to other proteins in high ionic strength solutions. Sephacryl S-200, a gel prepared by covalently cross-linking allyl dextran with N,N'-methylenebisacrylamide, also is commercially available from Pharmacia.

The amino acid analysis of the MOLT-4-derived SIRS, though showing substantial similarity with murine SIRS in content of some amino acids (for example, aspartic acid or asparagine, glutamic acid or glutamine, tyrosine and histidine), is distinctly different in content of certain other amino acids (namely, threonine, serine, glycine, alanine, arginine and methionine). The comparative amino acid analysis is set forth in Table 2 hereinafter.

The biological activity of MOLT-4 cell-derived SIRS is functionally similar to human urine-derived SIRS in certain aspects. Thus, the MOLT-4 cell-derived SIRS has similar characteristics in kinetics of suppression and in inhibition of its suppression by certain agents. The suppressive activity of the MOLT-4-derived SIRS can be determined in a standard plaque-forming cell (PFC) assay using human splenocytes. The splenocytes ($2 \times 10^6$/ml) can be cultured in RPMI 1640 medium supplemented with glutamine and 10% fetal calf serum together with penicillin and streptomycin antibiotics. Addition of as little as 1 to 3 μl of MOLT-4 cell supernatant to one ml of splenocyte culture significantly suppressed PFC responses. The MOLT-4-derived SIRS suppressed the PFC responses when added on day 0 of a 6-day splenocyte culture, but required activation to $SIRS_{ox}$ when added on day 5.

Suppression by MOLT-4 cell supernatant was inhibited by catalase, levamisole and 2-mercaptoethanol. Acidification of the MOLT-4- derived SIRS to pH 2 resulted in complete loss of suppressive activity as did treatment with protease.

The following examples will illustrate the invention in greater detail although it will be appreciated that the invention is not limited to these examples or the specific details recited therein.

EXAMPLE 1

The human T cell line MOLT-4 was cultured in RPMI 1640 medium containing 5 percent horse serum, penicillin/streptomycin antibiotics and glutamine to a concentration of about $1 \times 10^6$ cells/ml and a total volume of 17 liters. A combination of 5 μg/ml Concanavalin A, 5 μg/ml phorbol myristate acetate and 5 μg/ml cycloheximide was added to the cell culture. After four hours, 5 μg/ml actinomycin D was added. After one additional hour, cells were harvested by centrifugation, resuspended in complete RPMI 1640 medium containing 1 percent horse serum and cultrured for an additional 24 hours. At this time, the supernatant fluid was harvested by centrifugation and protein precipitated with 40 percent $(NH_4)_2SO_4$ at 0°-4° C. The precipitate was collected by centrifugation ($16,000 \times g$, 10 min), suspended in 0.025 M tris-HCl, pH 8.3, and dialyzed against the same buffer.

After dialysis, the protein-containing solution (900 ml) was clarified by centrifugation and applied to a column of DEAE Sephacyl® ($86 \times 2.5$ cm) equilibrated in 0.025 M tris-HCl, pH 8.3. Protein was eluted from the column with a linear gradient to 0.5 M NaCl in the above buffer. Fractions of 6.8 ml were collected. Protein content was determined by measuring optical density at 280 nm and SIRS activity was determined by bioassay. The vast majority of the protein eluted at greater than 0.22 M NaCl whereas all of the SIRS eluted between 0.11 and 0.16 M NaCl with a smaller peak of protein. Fractions containing SIRS bioactivity were pooled (fractions 51-75), dialyzed against water and lyophilized. This material was resuspended in 0.3 percent triethylamine adjusted to pH 5.0 with acetic acid, and SIRS was further purified by gel filtration using a Water's Protein Pac 125 column (silica gel). SIRS bioactivity was detected associated with a protein peak of about 15,000 daltons. Material from separate gel filtration steps with SIRS activity was pooled, lyophilized, suspended in 0.5 ml of the triethylamine buffer and loaded on a Vydac C-18 reverse phase HPLC column. Protein was eluted from the column with a linear 60 min gradient from 0 percent acetonitrile to 60 percent acetonitrile with a flow rate of 1 ml/min. Optical density was recorded at 254 nm and SIRS activity was determined by bio-assay. A single peak of protein was detected which eluted between 31 and 34 minutes which also contained all of the SIRS bioactivity.

Table 1 summarizes the purification of human SIRS from MOLT-4 cells. The total yield of SIRS protein was 75 μg and the specific activity, based on inhibition of division of human B-cell leukemia cells (RPMI 1788), was $3 \times 10^{11}$ units/mg protein. The yield of SIRS protein was difficult to evaluate due to the increase in total activity during the purification procedure. The increase appears to be due to removing inhibitors of SIRS activity during the purification. Increase of SIRS purity was a factor of approximately $10^8$.

Purity of human SIRS was assessed by SDS polyacrylamide gel electrophoresis (15 percent acrylamide). Human SIRS, as well as murine SIRS, does not stain well with conventional silver stain but stains well with Coomassie Brilliant Blue R dye. A single band was detected by either staining method at approximately 63,000 daltons. No additional bands were detected by silver staining. Migration of both human and murine SIRS at a high mol. wt. on SDS polyacrylamide gels is a reproducible observation. By contrast, murine SIRS has a mol. wt. of approximately 11,000 daltons and human SIRS has a mol. wt. of 15,000 daltons, as judged by gel filtration.

TABLE 1

Human Sirs Purification Summary

| Material | Protein[a] (mg) | SIRS (units)[b] | Specific activity (units/mg protein) |
|---|---|---|---|
| Supernatant | 15,000 | $8.5 \times 10^7$ | $5 \times 10^3$ |
| $(NH_4)_2SO_4$ precipitate | 2,600 | — | — |
| Ion exchange | 15 | $\geq 10^{10}$ | $6.7 \times 10^8$ |
| Gel filtration | 0.125 | $1 \times 10^{10}$ | $8 \times 10^{10}$ |
| Reverse phase HPLC | 0.075 | $2 \times 10^{10}$ | $3 \times 10^{11}$ |

[a]Protein concentration was determined by measuring optical density at 280 nm and assuming an extinction coefficient of 1.0 for a 1 mg/ml solution.
[b]SIRS activity was determined by bioassay.

TABLE 2

Amino acid composition of SIRS

| | Murine SIRS[a] | Human SIRS |
|---|---|---|
| Asx[b] | 9 | 9 |
| Threonine | 6 | 3 |
| Serine | 6 | 12 |
| Glx[b] | 13 | 12 |
| Glycine | 11 | 18 |
| Alanine | 12 | 6 |
| Valine | 8 | 6 |
| Methionine | 2 | 0 |
| Isoleucine | 5 | 3 |
| Leucine | 9 | 6 |
| Tyrosine | 3 | 3 |
| Phenylalanine | 4 | 3 |
| Histidine | 3 | 3 |
| Lysine | 5 | 3 |
| Arginine | 6 | 3 |
| Proline | —[c] | 0 |
| | aa/10,000 daltons | aa/10,000 daltons |

[a]Purified murine and human SIRS were hydrolyzed by 6M HCl/0.1 percent thioglycolic acid. A column buffer sample served as a blank and was subtracted from each protein sample.
[b]Includes both acid and amide forms; Asx = aspartic acid and asparagine; Glx = glutamic acid and glutamine.
[c]Not determined.

EXAMPLE 2

An alternate sequence to that in Example 1 for purification of SIRS from MOLT-4 cell culture is as follows:

Supernatant fluids containing SIRS were harvested by centrifugation and protein was precipitated with 40% $(NH_4)_2SO_4$. The protein precipitate was dialyzed against 0.025 M tris-HCl, pH 8.3, and loaded onto a column of DEAE-Sephacyl (6×50 cm) equilibrated in the same buffer. Protein was eluted with a linear gradient from 0.0 to 0.5 M NaCl. Fractions of 6.8 ml were collected and tested for SIRS bioactivity. Fractions with SIRS bioactivity were pooled, dialyzed against 0.025 M tris-HCl, pH 8.3, and loaded onto a Waters DEAE HPLC column. Protein was eluted with an increasing gradient of NaCl to 0.3 M. Fractions of 1 ml were collected and assayed for bioactivity. Fractions with SIRS bioactivity were pooled and fractionated by gel filtration with a Water's Protein-Pak 125 column and a silica resin in 0.2 M ammonium acetate, pH 5.0. Fractions of 1 ml were collected and assayed for bioactivity. Bioactive fractions were pooled and loaded onto a Vydac C-18 column and eluted with a linear gradient of 0–60% acetonitrile in 0.1% trifluoroacetic acid. Predominant protein and SIRS bioactive peaks eluted at 33–34% acetonitrile. Purity was judged by labeling SIRS protein with $^{125}I$ by the chloramine T method [Hunter and Greenwood, Biochem. J. 91, 46, (1964)] and fractionating labeled protein by SDS polyacrylamide gel electrophoresis. One protein band of approximately 63,000 daltons was observed by autoradiography. Mol. wt. of SIRS judged by gel filtration is 15,000 daltons in the absence of SDS. Addition of SDS causes aggregation of SIRS and an increase in mol. wt. to 63,000.

EXAMPLE 3

SIRS from MOLT-4 cells was further obtained and characterized as follows:

Production of SIRS by MOLT-4 Cells

The MOLT-4 cell line was maintained in RPMI 1640 medium supplemented with glutamine, pencillin/streptomycin, and 10 percent donor horse serum (KC Biologicals, Kansas City, MO). To obtain SIRS, cells were suspended at $5 \times 10^5$ cells/ml and cultured at 37° C. in round-bottomed sterile, plastic 12 ml culture tubes at 1.5 ml per tube, with or without varying doses of Con A (Sigma, St. Louis, MO) or IFN, in 5 percent $CO_2$ for 24 hours, then washed with Hank's balanced salt solution. The IFN was $IFN_\alpha A$ (Hoffman-LaRoche, Nutley, N.J.) or $IFN_\gamma A$ (Inteferon Sciences, Inc., New Brunswick, N.J.). After 24 hours, supernatant fluid was harvested by centrifugation and stored at 4° C. until use. To minimize possible complicating effects of adding horse serum to the PFC culture, the washed MOLT-4 cells were resuspended in the medium used for PFC cultures (containing fetal calf serum) for the time during which SIRS-containing supernatant was collected.

Fractionation of Supernatant Fluids

One ml of supernatant fluid was fractionated by gel filtration on a 1.75×27 cm (67.3 cm$^3$) column of Sephacryl S-200 (Sigma) in phosphate-buffered saline (PBS) or 0.4 M pyridine −0.4 M acetic acid buffer. The column was calibrated by using aldolase (158,000 daltons), bovine serum albumin (68,000 daltons), chymotrypsinogen A (25,000 daltons) and cytochrome C (13,000 daltons); the void volume was 16 ml. After the 2-ml fractions were collected and measured for protein content by absorption of 280 nm wavelength light, they were filter sterilized before testing in PFC cultures.

Reverse-phase HPLC was performed using an RP-8 analytical column (Lichrosorb, 10 μm, Darmstadt, FRG). The column was loaded with 1 ml of supernatant in a buffer of 1.0 M pyridine-0.5 M acetic acid and eluted with the same buffer containing an increasing gradient of n-propanol. Fractions were collected and lyophilized on a Speed-Vac Concentrator (Savant Instruments, Inc., Hicksville, N.Y.) to remove the pyridine-acetic acid, then resuspended in 1.5 ml PBS before filter sterilization. Protein concentration of HPLC fractions was determined by opitcal density at 280 nm or by the method of Lowry, J. Biol. Chem. 193, 265 (1951).

Functional properties of MOLT-4-derived SIRS

To suppress responses, human urine-derived SIRS must be activated to $SIRS_{ox}$ by peroxide. $SIRS_{ox}$ suppresses cell division and PFC responses when added to cultures several hours before assay, whereas SIRS must be added to splenocyte cultures at least 5 days before assay, presumably to allow for activation to $SIRS_{ox}$. Activation of human urine-derived SIRS is inhibited by catalase and levamisole, and $SIRS_{ox}$ is inactivated by 2-ME. To determine whether MOLT-4-derived SIRS shows similar characteristics, the kinetics of suppression and ability of agents which inhibit suppression by human urine-derived SIRS to inhibit suppression by MOLT-4 derived SIRS were tested. Table 3 shows the results of one of several similar tests. MOLT-4-derived SIRS suppressed responses when added on day 0 of a 6-day splenocyte culture, but required activation to $SIRS_{ox}$ to suppress responses when added on day 5. Suppression by MOLT-4 supernatant was inhibited by catalase, levamisole and 2-ME. These data show that MOLT-4-derived SIRS is functionally similar to human urine derived SIRS.

The PFC assay for determining the above functional properties of MOLT-4-derived SIRS was carried out as follows:

Cultures for Human PFC Assay

Human splenocytes ($2 \times 10^6$/ml), or peripheral blood mononuclear cells (PBMC) ($2 \times 10^6$/ml), were cultured in RPMI 1640 medium supplemented with glutamine, penicillin/streptomycin, nonessential amino acids, and 10 percent fetal calf serum (lot 60808, Reheis Chemical Co., Phoenix, AZ). Cultures of 1 ml were incubated with pokeweed mitogen (PWM), 5 µg/ml, in 24-well, flat bottomed plates (Flow Laboratories, Hamden, Conn.) in humidified, 5 percent $CO_2$ in air for 6 days. At the end of this period cultured cells were washed, resuspended in Hanks's balanced salt solution containing penicillin streptomycin and 2 percent fetal calf serum, and assayed for immunoglobulin production in a slide modification of the Jerne Hemolytic PFC assay as described by Gronowicz et al., *Eur. J. Immunol.* 6, 588 (1976). As described previously by Schnaper, Aune and Pierce, *J. Immunol.* 131, 2301 (1983), indirect polyclonal IgM PFC responses were measured using staphyloccal protein A-coated sheep erythrocytes, rabbit anti-human IgM antiserum (Boehringer-Mannheim Biochemicals, Indianapolis, Ind.), and guinea pig complement (Rockland, Gilbertsville, Pa.). Cultures without mitogen contained less than 10 percent of the PFC found in stimulated controls; these background responses were not subtracted from experimental results. Each test was performed at least twice; representative results are shown in Table 3 below.

TABLE 3

| Functional characterization of MOLT-4-derived SIRS* | | | |
|---|---|---|---|
| MOLT-4 supernatant added | Day added | Inhibitor | PFC/culture |
| None | — | — | 3160 |
| Factor | 0 | — | 1020 |
| Factor | 5 | — | 3060 |
| Factor$_{ox}$** | 5 | — | 1480 |
| Factor | 0 | Levamisole, 5 µg/ml | 3965 |
| Factor | 0 | Catalase, 5,000 I.U. | 2975 |
| Factor | 0 | 2-ME, $10^{-4}$M | 3380 |

*Factor was added to pokeweed mitogen-stimulated splenocyte cultures which were assayed for PFC response after 6 days in culture. Factor = MOLT-4 supernatant.

**Supernatant in this experimental group was reacted with $H_2O_2$ at a final concentration of $1 \times 10^{-6}$ M for 20 min. at 4° C. before addition to culture. Medium reacted with $10^{-6}$ M $H_2O_2$ before being added on day 5 did not affect responses.

Physical properties of MOLT-4-derived SIRS

Figure 1:
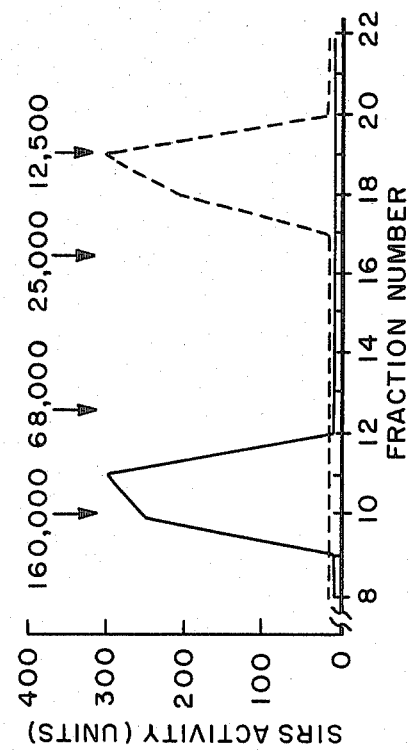
FIG. 1 is a graphical representation which shows the elution profile of the culture supernatant of Con A-treated MOLT-4 cells fractionated by gel chromatography with Sephacryl S-200.

To estimate the molecular weight of SIRS obtained from MOLT-4 cells, 1 ml of supernatant was fractioned by gel chromatography with Sephacryl S-200. FIG. 1 depicts the results of one series of tests evaluating factor from Con A-treated cells. Suppressive activity was eluted in PBS in the fractions preceding the albumin peak, corresponding to the molecular weight of 110,000–160,000 daltons, as demonstrated for human lymphocyte-derived SIRS, Schnaper, Pierce and Aune, *J. Immunol.* 132, 2429 (1984). When chromatography of similar supernatant of urine-derived SIRS was performed using 0.4 M pyridine-0.4 M acetic acid as the elution buffer, the molecular weight was estimated to be 10,000–15,000. Schnaper and Aune, *J. Clin. Invest.* 76, 341 (1985). These results were invariable through multiple determinations regardless of whether Con A or IFNαA was used to treat the MOLT-4 cells. The apparent shift in molecular weight is characteristic of both murine and human SIRS and is believed to represent decreased aggregation or binding of SIRS to other proteins in high ionic strength solutions.

Urine-derived human SIRS is inactivated by acidification to pH 2, or treatment with protease. In the test shown in Table 4, acidification of SIRS from Con A-stimulated MOLT-4 cell cultures to pH 2 resulted in complete loss of suppressive activity. Protease treatment also abolished suppression. Similar results in other tests confirms that MOLT-4-derived SIRS is, like human urine-derived SIRS, both acid- and protease-sensitive.

HPLC of MOLT-4-derived SIRS

Figure 2:
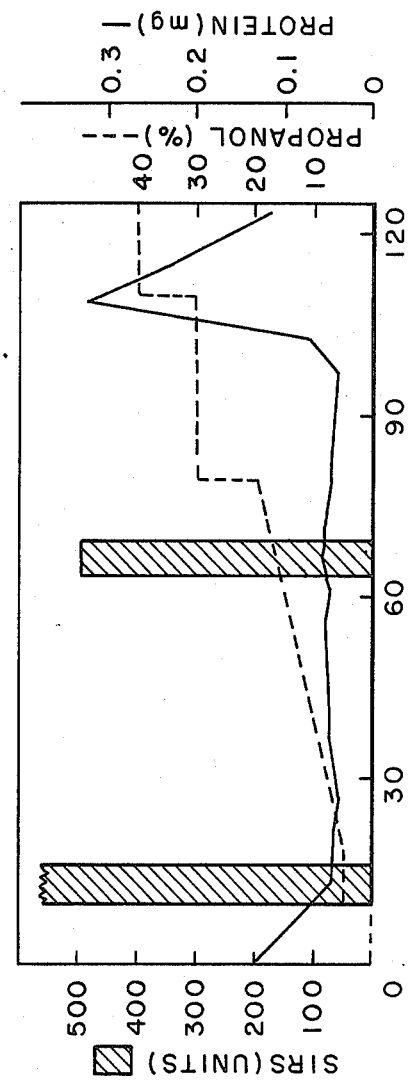
FIG. 2 is a graphical representation which shows the elution profile of the culture supernatant of Con A-treated MOLT-4 cells subjected to RP-HPLC.

Further physical characterization of MOLT-4-derived SIRS was performed by reverse-phase HPLC of culture supernatant fluid on an RP-8 analytical column using an increasing gradient of n-propanol to elute protein. A representative test using supernatant from Con A-treated MOLT-4 cells is depicted in FIG. 2. As with urine-derived human SIRS, all suppressive activity bound to the column, and two major peaks of activity were eluted from the column at the step-up to 5 percent propanol and at 18–19 percent propanol on the linear gradient. Further increases to 60 percent propanol did not result in elution of additional activity. An identical elution pattern was found with HPLC of IFN-treated cell supernatants, and indicates that MOLT-4-derived SIRS is structurally similar to human urine-derived SIRS.

TABLE 4

Effect of acid or protease treatment of MOLT-4 culture supernatant on suppressive activity*

| Factor Treatment** | PFC/culture |
|---|---|
| No Factor Added | 6120 |
| Unreacted Factor | 3020 |
| pH 4 | 2600 |
| pH 2 | 9360 |
| Protease*** | 8920 |

*Factor (1 μl) was added to 1 ml PWM-stimulated splenocyte cultures on day 1 of a 6-day culture period.
**Factor was acidified to pH 4 or pH 2 with HCl, then neutralized with NaOH after 3 hr. at 4° C. Alternatively, urine was incubated with protease, 10 μg/ml for 1 hour before addition to culture.
***Proteinase K from *Tritirachium album* (Sigma)

Various other examples will be apparent to the person skilled in the art after reading the present disclosure without departing from the spirit and scope of the invention and it is intended that all such other examples be included within the scope of the appended claims.

What is claimed is:

1. Human soluble immune response suppressor having suppressive activity against lymphocyte cells, being activated by peroxide, inactivated by protease and acid, inhibited by catalase, levamisole and 2-mercaptoethanol, having a molecular weight of about 10,000 to 15,000 as determined by gel chromatography on a Sephacryl column using an elution buffer of 0.4 M pyridine and 0.4 M acetic acid, an isoelectric point of about 7 and a partial amino acid composition of about as follows:

| Amino Acid | Residues |
|---|---|
| Asx | 9 |
| Thr | 3 |
| Ser | 12 |
| Glx | 12 |
| Gly | 18 |
| Ala | 6 |
| Val | 6 |
| Met | 0 |
| Ile | 3 |
| Leu | 6 |
| Tyr | 3 |
| Phe | 3 |
| His | 3 |
| Lys | 3 |
| Arg | 3 |
| Pro | 0. |

2. A method of producing human soluble immune response suppressor as defined in claim 1 comprising culturing MOLT-4 cells in nutrient culture medium at 37° C. and recovering the resulting soluble immune response suppressor therefrom.

3. The method of claim 2 in which the human soluble immune response suppressor is recovered after a culture period of at least 12 hours by subjecting a supernate of the MOLT-4 cell culture medium to 40% ammonium sulfate precipitation, ion exchange chromatography, gel filtration chromatography and high performance liquid chromatography.

* * * * *